United States Patent
Dehe et al.

(10) Patent No.: US 10,194,226 B2
(45) Date of Patent: Jan. 29, 2019

(54) DEVICE FOR DETECTING ACOUSTIC WAVES

(71) Applicant: Infineon Technologies AG, Neubiberg (DE)

(72) Inventors: Alfons Dehe, Reutlingen (DE); David Tumpold, Kirchheim (DE); Gueclue Onaran, Munich (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

(21) Appl. No.: 15/587,535

(22) Filed: May 5, 2017

(65) Prior Publication Data

US 2017/0325013 A1  Nov. 9, 2017

(30) Foreign Application Priority Data

May 6, 2016 (DE) .................... 10 2016 108 421

(51) Int. Cl.

| H04R 1/04 | (2006.01) |
|---|---|
| H04R 19/04 | (2006.01) |
| H04R 29/00 | (2006.01) |
| G01N 29/02 | (2006.01) |
| G01N 29/24 | (2006.01) |
| H04R 1/08 | (2006.01) |

(52) U.S. Cl.
CPC ............. *H04R 1/04* (2013.01); *G01N 29/02* (2013.01); *G01N 29/2418* (2013.01); *H04R 1/08* (2013.01); *H04R 19/04* (2013.01); *H04R 29/004* (2013.01); *H04R 2201/003* (2013.01); *H04R 2201/029* (2013.01)

(58) Field of Classification Search
CPC . H04R 1/04; H04R 1/08; H04R 19/04; H04R 29/004; H04R 2201/003; H04R 2201/029; G01N 29/02; G01N 29/2418
USPC ........................................... 381/174
See application file for complete search history.

(56) References Cited

U.S. PATENT DOCUMENTS

| 5,627,901 A | 5/1997 | Josephson et al. |
|---|---|---|
| 6,157,476 A | 12/2000 | Angerstein et al. |
| 6,781,231 B2 * | 8/2004 | Minervini ............. B81B 7/0064 |
| 8,102,015 B2 * | 1/2012 | Gong .................... B81C 1/0023 |
| | | 257/416 |
| 9,002,038 B2 * | 4/2015 | Ochs ....................... H04R 23/00 |
| | | 381/174 |

(Continued)

FOREIGN PATENT DOCUMENTS

| CN | 202334881 | * 7/2012 | ............. H04R 19/04 |
|---|---|---|---|
| DE | 4103784 A1 | 8/1991 | |

(Continued)

OTHER PUBLICATIONS

Wikipedia, "Wärmeleitfähigkeit" website, https://de.wikipedia.org/wiki/W%C3%A4rmeleitf%C3%A4higkeit, Apr. 23, 2016 (documents obtained on May 4, 2017), p. 1-5.

*Primary Examiner* — Oyesola C Ojo
(74) *Attorney, Agent, or Firm* — Viering, Jentschura & Partner MBB

(57) ABSTRACT

A device for detecting acoustic waves may include a housing having a housing wall with an inner surface, and an acoustic wave sensor provided at least partially inside the housing and configured to detect acoustic waves. The inner surface of the housing wall is made in at least half of its entire area of a thermally insulating material.

24 Claims, 3 Drawing Sheets

(56) References Cited

U.S. PATENT DOCUMENTS

| | | | | |
|---|---|---|---|---|
| 9,445,212 B2* | 9/2016 | Chen | ............... | H04R 31/00 |
| 2004/0114272 A1* | 6/2004 | Rathweg | ............... | G11B 23/107 |
| | | | | 360/93 |
| 2007/0158826 A1* | 7/2007 | Sakakibara | ............ | B81B 7/0064 |
| | | | | 257/723 |
| 2008/0164592 A1* | 7/2008 | Bakke | ................ | B81B 7/0067 |
| | | | | 257/680 |
| 2009/0142065 A1 | 6/2009 | Kreusser | | |
| 2009/0267223 A1* | 10/2009 | Wachtler | ............ | B81B 7/0077 |
| | | | | 257/710 |
| 2010/0285628 A1* | 11/2010 | Martin | ............... | B81C 1/00182 |
| | | | | 438/53 |
| 2011/0298064 A1* | 12/2011 | Pahl | ............... | B81B 7/0048 |
| | | | | 257/415 |
| 2012/0243721 A1* | 9/2012 | Inoda | ................ | H04R 3/005 |
| | | | | 381/365 |
| 2013/0100779 A1* | 4/2013 | Lee | ............... | H04R 31/00 |
| | | | | 367/188 |
| 2013/0221468 A1* | 8/2013 | Bolognia | ............ | H01L 31/024 |
| | | | | 257/433 |
| 2015/0256917 A1* | 9/2015 | Schelling | ............... | H04R 1/08 |
| | | | | 381/111 |
| 2016/0126111 A1* | 5/2016 | Leipold | ............... | H01L 23/315 |
| | | | | 438/126 |
| 2016/0212549 A1* | 7/2016 | Liu | ............... | H04R 19/04 |

FOREIGN PATENT DOCUMENTS

| | | |
|---|---|---|
| DE | 19653793 A1 | 6/1998 |
| DE | 102006014848 A1 | 10/2007 |
| DE | 102010026519 A1 | 1/2012 |
| DE | 102011002460 A1 | 7/2012 |
| DE | 102011004570 A1 | 8/2012 |
| DE | 102014203881 A1 | 9/2015 |

* cited by examiner

DEVICE FOR DETECTING ACOUSTIC WAVES

CROSS-REFERENCE TO RELATED APPLICATION

This application claims priority to German Patent Application Serial No. 10 2016 108 421.2, which was filed May 6, 2016, and is incorporated herein by reference in its entirety.

TECHNICAL FIELD

Various embodiments relate generally to a device for detecting acoustic waves including a housing and an acoustic wave sensor.

BACKGROUND

A key performance parameter of sensors in general is the signal-to-noise ratio which is directly linked to both the sensitivity and the resolution of the sensors. This also applies to devices for detecting acoustic waves. Low noise levels are a mandatory prerequisite for achieving high signal-to-noise ratios.

A specific noise source of devices for detecting acoustic waves arises from thermal fluctuations of gas present inside the housing that induce pressure fluctuations, i.e. acoustic waves, that may contribute to the noise level of the device.

SUMMARY

According to various embodiments, a device for detecting acoustic waves is provided. The device may include a housing having a housing wall with an inner surface, and an acoustic wave sensor provided at least partially inside the housing and configured to detect acoustic waves. The inner surface of the housing wall is made in at least half of its entire area of a thermally insulating material.

According to various embodiments, a device for detecting acoustic waves is provided. The device may include a housing having a metal housing portion, a layer formed on an inner surface of the metal housing portion, and an acoustic wave sensor provided at least partially inside the housing and configured to detect acoustic waves. The layer is made of a material having a thermal conductivity that is smaller than the thermal conductivity of the metal housing portion.

According to various embodiments, a device for detecting acoustic waves is provided. The device may include a housing having a housing wall, and an acoustic wave sensor provided at least partially inside the housing and configured to detect acoustic waves. The housing wall comprises a portion extending from the inner surface to the outer surface of the housing wall, the portion being entirely made of a thermally insulating material.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which.

DESCRIPTION

The following detailed description refers to the accompanying drawings that show, by way of illustration, specific details and embodiments in which the invention may be practiced.

The word "exemplary" is used herein to mean "serving as an example, instance, or illustration". Any embodiment or design described herein as "exemplary" is not necessarily to be construed as preferred or advantageous over other embodiments or designs.

Figure 1:
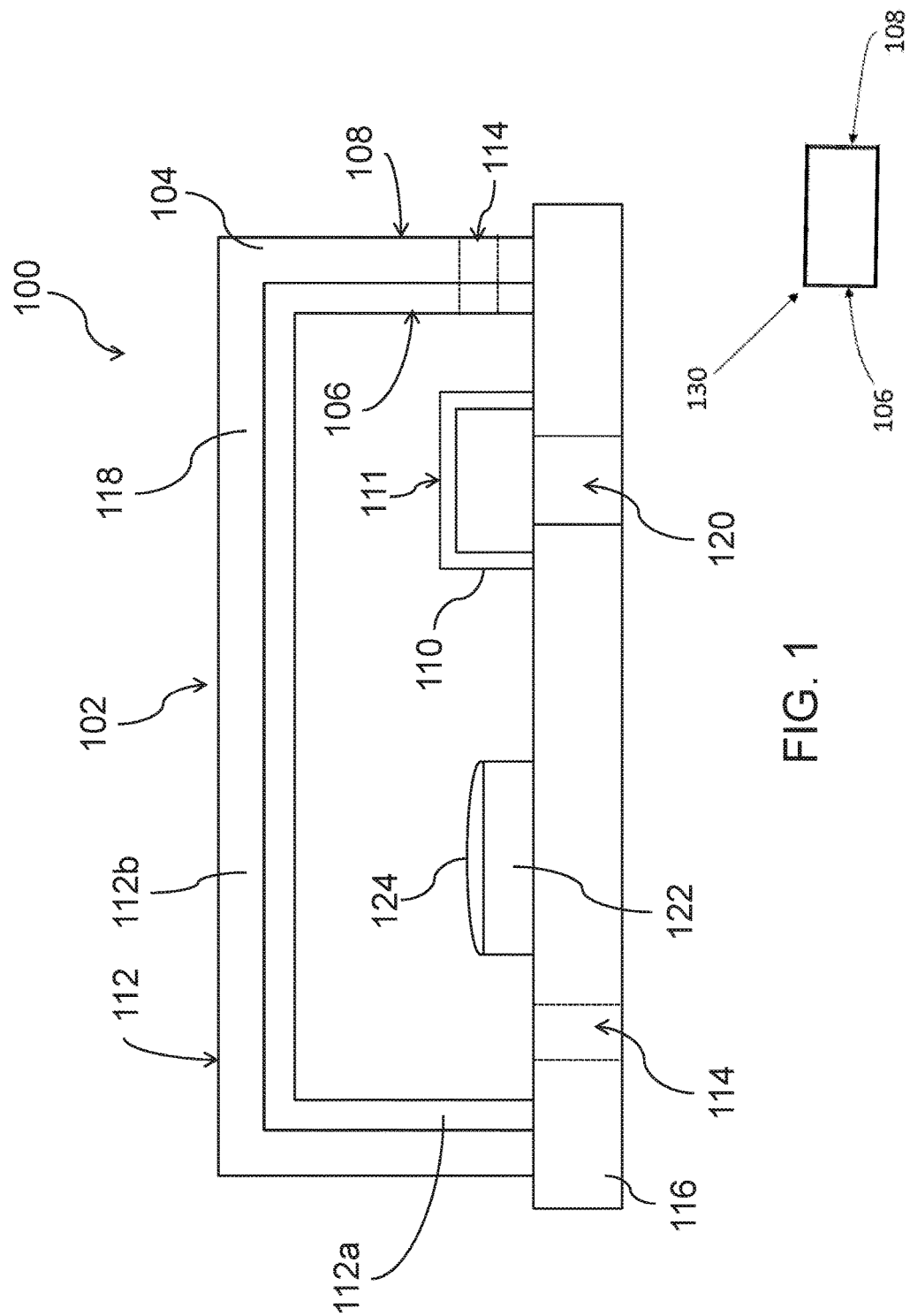
FIG. 1 shows a schematic view of a device for detecting acoustic waves.

FIG. 1 shows a device 100 for detecting acoustic waves. The device may include a housing 102 having a housing wall 104 with an inner surface 106 and an outer surface 108. The device 100 may include an acoustic wave sensor 110 provided at least partially inside the housing 102 and configured to detect acoustic waves. As indicated in FIG. 1, the sensor 110 may include a membrane 111 that may be caused to vibrate by the acoustic waves to be detected, thereby generating a detection signal indicative of the acoustic wave energy and/or intensity. The inner surface 106 of the housing wall 104 may be made in at least half of its entire area of a thermally insulating material.

Thermally induced noise in devices for detecting acoustic waves may be generated by a time-varying energy input into the inside of the housing 102 leading to a temperature rise of gas present inside the housing 102 and thereby to an increase in gas pressure. The time-varying energy input may either originate from the exterior of the housing or from an isothermal heat exchange with a lining at the inner surface of the housing wall made of a material with a high thermal conductivity such as metal. The temperature of the gas may be thereby increased above the temperature of a heat sink to which the housing 102 is coupled via a thermal link. Such a heat sink may be a holder of the device 100 or the surrounding atmosphere. Via the thermal link a heat exchange subsequently occurs with the heat sink after the energy input into the inside of the housing 102, thereby reducing the temperature of the gas inside the housing 102 and, hence, its pressure. This in turn leads to pressure fluctuations of the gas inside the housing 102, i.e. to acoustic waves that may be detected as noise by the acoustic wave sensor 110.

By making the inner surface 106 of the housing wall 104 in at least half of its entire area of a thermally insulating material, the thermal link between the interior of the housing 102 and the exterior of the housing 102 that may act as a heat sink is reduced as compared to housings entirely made of metal which is generally the case in common devices for detecting acoustic waves. In this way, the frequencies of pressure fluctuations of the gas inside the housing 102 induced by a time-varying energy input into the interior of the housing 102 can be reduced compared to common metal housings, thereby shifting the frequency of the thermally induced noise to lower frequencies, e.g. outside of the frequency range of a signal to be detected by the acoustic wave sensor 110. Consequently, the signal-to-noise ratio of the device 100 can be improved, since the noise power in the frequency range of the signal is reduced.

The acoustic wave sensor 110 may be configured as a microphone, e.g. a microphone employed in a telephone such as a MEMS microphone. In this case, the frequency range of the signal to be detected by the acoustic wave sensor 110 is the audible frequency range (about 20 Hz to about 20 kHz). Here, the frequencies of the thermally induced noise may be shifted down to below 20 Hz, i.e. outside of the audible frequency range, thereby reducing the noise in the frequency range of the signal and increasing the signal-to-noise ratio of the microphone.

The frequency range of the signal is the frequency range between the lowest and the highest frequency components of the signal. The frequency components of the signal may be determined by Fourier transformation or any other suitable spectral transformation.

The suppression of thermally induced noise in the device 100 for detecting acoustic waves may be the more efficient the lower the thermal conductivity of the thermally insulating material is. The thermal conductivity of the thermally insulating material may be less than about 20 W/(m·K) or even less than about 10 W/(m·K). In an exemplary device, the thermal conductivity of the thermally insulating material may be even less than about 5 W/(m·K). The thermal conductivity of the thermally insulating material can be as low as about 0.02 W/(m·K) which nearly corresponds to the thermal conductivity of air. Such a low thermal conductivity may be achieved, e.g., with expanded polystyrene that relies on thermal insulation by air. An even lower thermal conductivity may be provided by a vacuum shield that may be microfabricated.

In an exemplary device 100, the housing wall 104 may have a portion 130 (see FIG. 1) extending between the inner surface 106 and the outer surface 108 of the housing wall 104, the portion 130 being entirely made of the thermally insulating material. This means that this portion 130 extends over the full thickness of the housing wall 104. Another parameter that may directly influence the suppression of thermally induced noise may be the area of the inner surface 106 that is made of the thermally insulating material. The suppression of thermally induced noise may be the more efficient the higher the area of the inner surface 106 of the housing wall 104 made of the thermally insulating material is. The inner surface 106 of the housing wall 104 may be made in at least 70% or even in at least 90% of its entire area of the thermally insulating material. In an exemplary device 100 for detecting acoustic waves, the entire inner surface 106 of the housing wall 104 may be made of the thermally insulating material.

As shown in FIG. 1, the housing wall 104 may include a layered portion 112. The layered portion 112 may include a plurality of layers 112a, 112b stacked in a thickness direction of the housing wall 104. The layered portion 112 may include an inner layer 112a forming at least a part of the inner surface 106 of the housing wall 104, and at least one outer layer 112b positioned closer to the outer surface 108 of the housing wall 104 than the inner layer 112a.

Although the device 100 shown in FIG. 1 includes a layered portion 112 with only two layers 112a, 112b, layered portions 112 with more than two layers are also conceivable.

The inner layer 112a may be made at least in part of the thermally insulating material.

In various embodiments, one outer layer 112b may be made at least in part of a material having a higher thermal conductivity than the material of the inner layer 112a. The outer layer 112b may be made of an electrically conductive material such as a metal to support EMI (electromagnetic interference) protection. The outer layer 112b made of a material with a higher thermal conductivity may form at least a part of the outer surface 108 of the housing wall 104.

The device 100 for detecting acoustic waves does not necessarily have to be employed in a telephone. An exemplary device 100 for detecting acoustic waves may be employed in a gas analyzer configured to analyze gases based on the photo-acoustic effect. In such a gas analyzer, a gas to be analyzed is excited by an excitation radiation such as light, e.g. emitted by a laser e.g. in the visible or in the ultraviolet (UV) frequency range in a time-varying fashion. Infrared (IR) excitation radiation is also conceivable. The energy of the excitation radiation may be chosen depending on particles that are to be detected in the gas to be analyzed. In various embodiments, the frequency may be chosen to match an atomic or molecular transition characteristic to certain particles to be detected in the analyzed gas. In this way, these particles can be selectively excited by the excitation radiation.

During the subsequent relaxation of the excited atomic or molecular energy states, thermal energy is generated. Since the gas to be analyzed is excited in a time-varying fashion, e.g. periodically, thermal energy is also generated in a time-varying fashion leading to pressure fluctuations in the gas, i.e. acoustic waves that may be detected by the acoustic wave sensor 110.

The gas to be analyzed may be received inside the housing 102 of the device 100 shown in FIG. 1. The excitation radiation may be supplied to the gas to be analyzed inside the housing 102 through one or more optically transparent window portions 114 provided in the housing wall 104.

By selecting the energy of the excitation radiation to match a characteristic atomic or molecular transition energy of particles to be detected in the analyzed gas, the amount of acoustic energy generated during the relaxation of the excited states and detected by the acoustic wave sensor 110 is indicative of a certain content of the particles to be detected in the analyzed gas.

To avoid a temperature rise of the housing wall 104, e.g. by the excitation radiation, the inner layer 112a may be made at least in part or even entirely of a material which is optically transparent. Depending, e.g. on the frequency of the excitation radiation in case of a gas analyzer, the optically transparent material may be optically transparent in the infrared and/or in the visible and/or in the ultraviolet frequency range.

In an exemplary device, the optically transparent material may have a transmittance of at least about 80% or even of at least about 90% in the infrared and/or in the visible and/or in the ultraviolet frequency range.

In order to inhibit or reduce the input of electromagnetic radiation into the housing 102 from the exterior of the housing 102, at least one outer housing wall layer 112b may be made at least in part or entirely of a material which is optically opaque. In case of a gas analyzer, an opaque outer housing wall layer 112b may also avoid losses of excitation radiation through the housing wall 104.

The optically opaque material may be optically opaque in the infrared and/or in the visible and/or in the ultraviolet frequency range.

The optically opaque material may have a reflectance of at least about 80% or even of at least about 90% in the infrared and/or the visible and/or in the ultraviolet frequency range. This may be achieved with an outer layer 112b made at least in part or entirely of a metal.

An exemplary device 100 configured as a gas analyzer may have an inner layer 112a made of an optically transparent material with a low thermal conductivity as defined above, and an outer layer 112b acting as a reflector to provide an efficient gas excitation.

As shown in FIG. 1, the housing 102 may include a substrate 116 on which the acoustic wave sensor 110 is mounted, and a lid 118. Thus the housing wall 104 may also be comprised of the substrate 116 and the lid 118. The substrate 116 may be made of a semiconductor such as silicon. The lid 118 may include a part of the layered portion 112 of the housing wall 102 or may be even identical to the layered portion 112 of the housing wall 102.

The substrate 116 may include an acoustic port 120 in close proximity to the mounting position of the acoustic wave sensor 110 to efficiently direct acoustic waves to the acoustic wave sensor 110.

In order to provide an efficient suppression of thermally induced noise, at least a part of the substrate 116 facing to the inside of the housing 102 may be coated with a thermally insulating substrate material. In other words, a part of the substrate 116 or the entire surface of the substrate 116 facing to the inside of the housing 102 may be coated with a thermally insulating substrate material.

The thermal conductivity of the thermally insulating substrate material may be less than about 20 W/(m·K) or even less than about 10 W/(m·K). In an exemplary device, the thermal conductivity of the thermally insulating substrate material may be even less than about 5 W/(m·K).

Besides the acoustic wave sensor 110, the substrate 116 may also include an electronic circuit 122 mounted thereon inside the housing 102, e.g. for processing signals such as electric signals generated by the sensor 110, e.g. by its vibrating membrane 111. In order to provide an efficient suppression of thermally generated noise, the electronic circuit 122 may be at least in part coated with thermally insulating substrate material 124.

The electronic circuit 122 may include a printed circuit board and/or an electronic component such as an application specific integrated circuit (ASIC). The thermally insulating substrate material may be coated on a surface of the printed circuit board and/or of the electronic component. Thermally insulating material may be also provided on the membrane 111 of the sensor 110 and/or on bonding wires.

In an exemplary device 100, no open metallization is present inside the housing 102, e.g. no open metallization of the electronic circuit 122. This may be achieved by avoiding any bonding wires inside the housing 102, e.g. by providing electrical contacts by flip-chip bonding inside the housing 102.

The thermally insulating material of the housing wall 104 and/or the thermally insulating material on the substrate 116 may be selected from glass materials, plastic materials such as polymers, Teflon or a mold compound, and oxides such as metal oxides.

It should be noted that the inner surface 106 of the housing wall 104 may be made in different portions of different thermally insulating materials. Also the substrate 116 or the components mounted thereon may be coated in different portions thereof with different thermally insulating materials.

The configuration shown in FIG. 1 with the sensor 110 mounted on the substrate 116 and the acoustic port 120 provided in the substrate 116 is referred to as "bottom-port" configuration.

Figure 2:
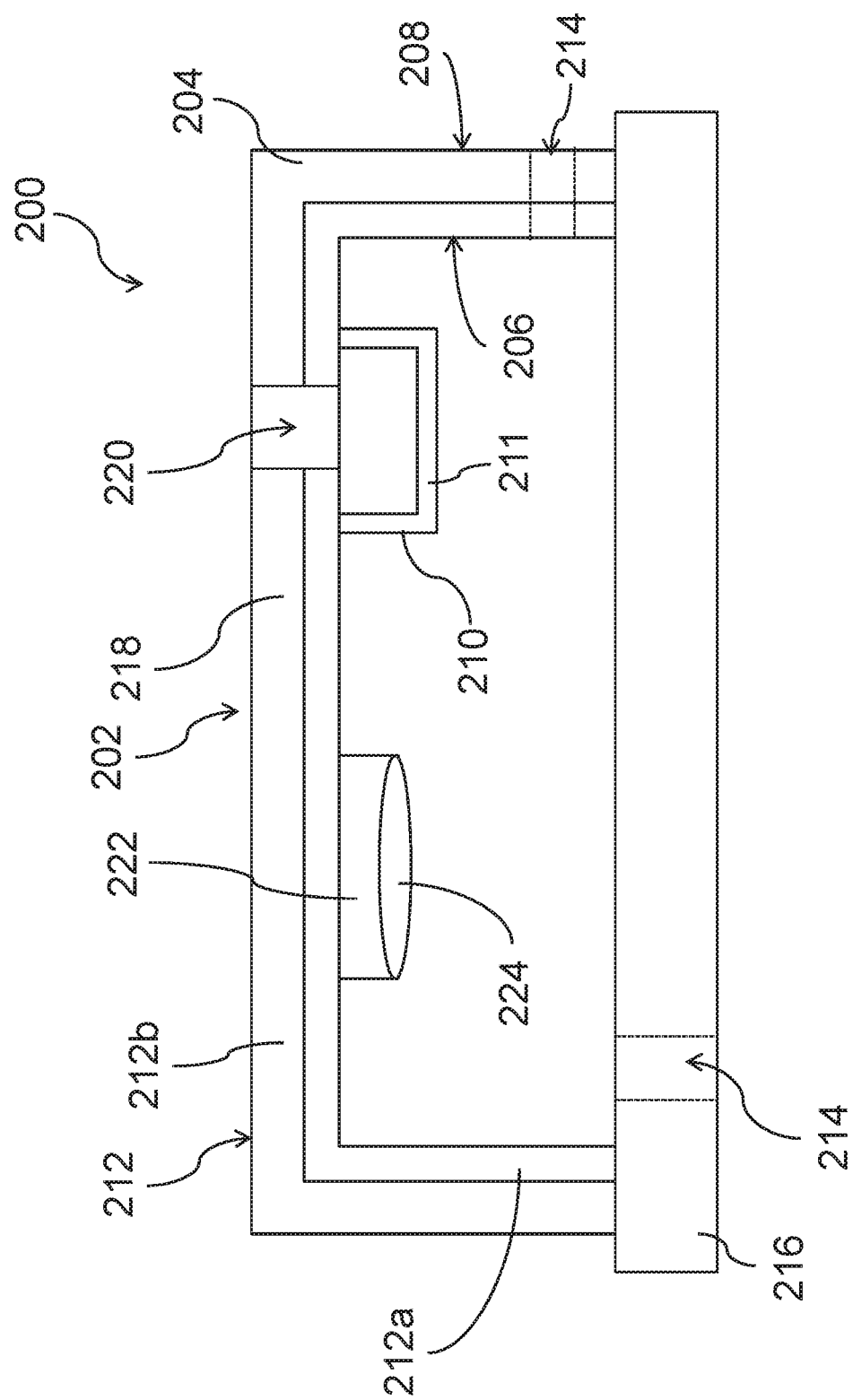
FIG. 2 shows a schematic view of a modified device for detecting acoustic waves.

A device 200 for detecting acoustic waves according to a mirrored configuration with an acoustic wave sensor 210 mounted on a lid 218 and an acoustic port 220 provided in the lid 218 is shown in FIG. 2. This configuration is referred to as "top-port" configuration. In FIG. 2 the same reference numerals are used for the same elements as in FIG. 1, however, enhanced by the number 100.

In the exemplary device shown in FIG. 2 also an electronic component 222 is mounted on the lid 218. In this way, the length of wires between an acoustic wave sensor 210 and the electronic component 222 can be kept short, thereby reducing their contribution to the overall thermal conductivity of the thermal link between the interior and the exterior of the housing 102.

The above concepts described with respect to device 100 according to the "bottom-port" configuration apply also to the device 200 shown in FIG. 2 according to the "top-port" configuration.

Figure 3:
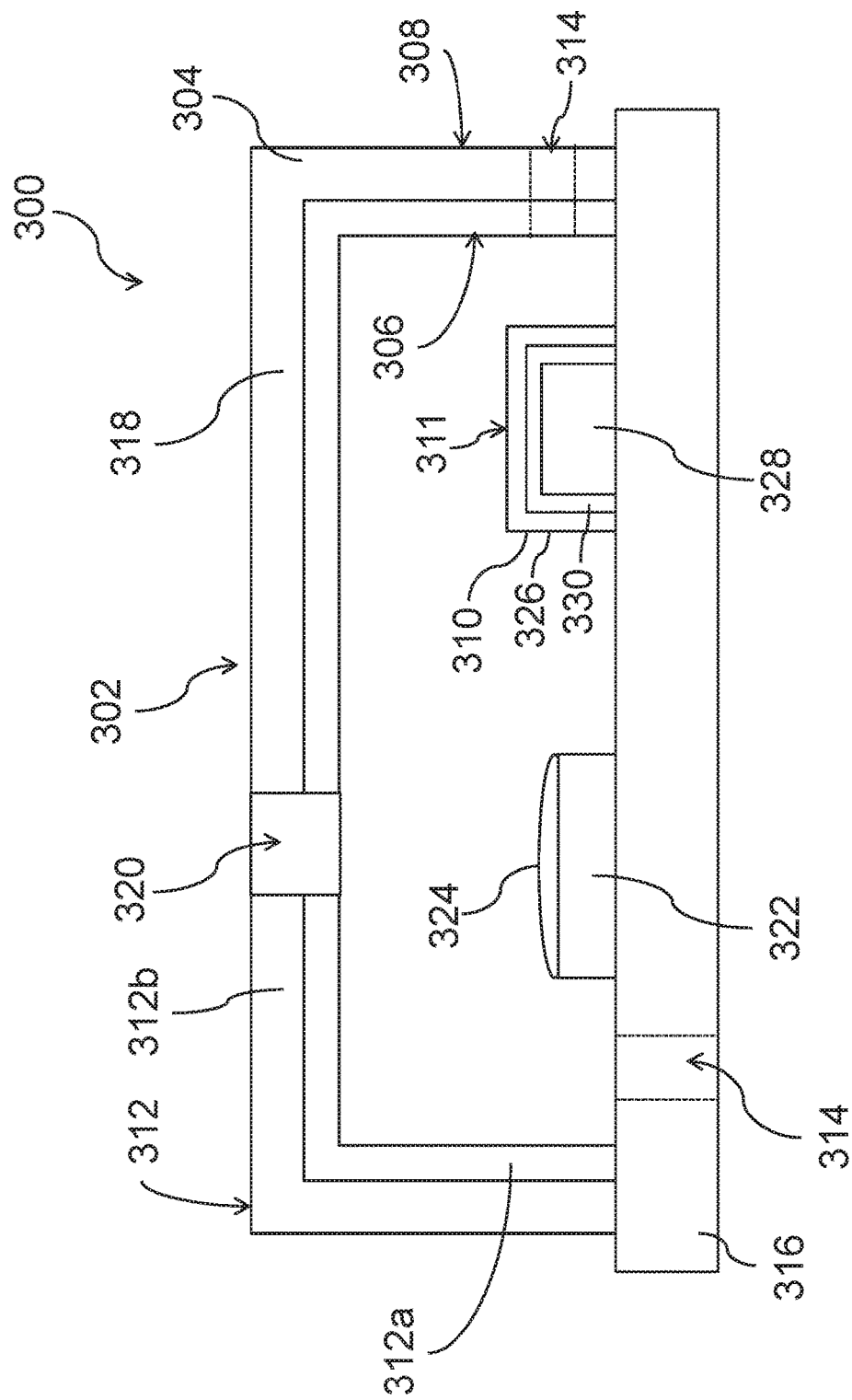
FIG. 3 shows a schematic view of another modified device for detecting acoustic waves.

A modified device 300 for detecting acoustic waves according to the "top-port" configuration is shown in FIG. 3. In FIG. 3 the same reference numerals are used for the same elements as in FIG. 1, however, enhanced by the number 200.

The exemplary device 300 shown in FIG. 3 differs from the device shown in FIG. 1 in that the acoustic port 320 is provided in the lid 318. Similar to the device 100 of FIG. 1, the electronic component 322 and the acoustic wave sensor 310 are mounted on the substrate 316.

In the configuration shown in FIG. 3, walls 326 of the acoustic wave sensor 310 define with the substrate 316 an enclosed volume 328 that might be the origin of the above-discussed noise.

In order to suppress this kind of noise, the walls 326 of the acoustic wave sensor 310 may include thermally insulating material 330 at a side thereof delimiting the enclosed volume 328. The thermally insulating material may include the above-described thermally insulating materials, e.g. oxides and polymers.

The other concepts described with respect to the device 100 shown in FIG. 1 apply also to the device 300 shown in FIG. 3.

In the following, various aspects of this disclosure will be illustrated:

Example 1 is a device for detecting acoustic waves. The device may include a housing having a housing wall with an inner surface, and an acoustic wave sensor provided at least partially inside the housing and configured to detect acoustic waves. The inner surface of the housing wall is made in at least half of its entire area of a thermally insulating material.

In Example 2, the subject matter of Example 1 can optionally include that the thermal conductivity of the thermally insulating material is less than 20 W/(m·K).

In Example 3, the subject matter of Example 2 can optionally include that the thermal conductivity of the thermally insulating material is less than 10 W/(m·K).

In Example 4, the subject matter of Example 3 can optionally include that the thermal conductivity of the thermally insulating material is less than 5 W/(m·K).

In Example 5, the subject matter of any one of Examples 1 to 4 can optionally include that the inner surface of the housing wall is made in at least 70% of its entire area of the thermally insulating material.

In Example 6, the subject matter of Example 5 can optionally include that the inner surface of the housing wall is made in at least 90% of its entire area of the thermally insulating material.

In Example 7, the subject matter of any one of Examples 1 to 6 can optionally include that the housing wall includes a layered portion including a plurality of layers stacked in a thickness direction of the housing wall. The layered portion may include an inner layer forming at least a part of the inner surface of the housing wall, and at least one outer layer positioned closer to an outer surface of the housing wall than the inner layer.

In Example 8, the subject matter of Example 7 can optionally include that the inner layer is made at least in part of the thermally insulating material.

In Example 9, the subject matter of Example 8 can optionally include that at least one outer layer is made at least in part of a material having a higher thermal conductivity than the material of the inner layer.

In Example 10, the subject matter of Example 9 can optionally include that one outer layer forming at least a part of the outer surface of the housing wall has a higher thermal conductivity than the inner layer.

In Example 11, the subject matter of any one of Examples 9 or 10 can optionally include that at least one outer layer is made at least in part of a metal.

In Examples 12, the subject matter of any one of Examples 7 to 11 can optionally include that the inner layer is made at least in part of a material which is optically transparent.

In Example 13, the subject matter of Example 12 can optionally include that the optically transparent material is optically transparent in the infrared and/or in the visible and/or in the ultraviolet frequency range.

In Example 14, the subject matter of Example 13 can optionally include that the optically transparent material has a transmittance of at least 80% in the infrared and/or in the visible and/or in the ultraviolet frequency range.

In Example 15, the subject matter of Example 14 can optionally include that the optically transparent material has a transmittance of at least 90% in the infrared and/or in the visible and/or in the ultraviolet frequency range.

In Example 16, the subject matter of any one of Examples 7 to 15 can optionally include that at least one outer layer is made at least in part of a material which is optically opaque.

In Example 17, the subject matter of Example 16 can optionally include the optically opaque material is optically opaque in the infrared and/or in the visible and/or in the ultraviolet frequency range.

In Example 18, the subject matter of Example 17 can optionally include that the optically opaque material has a reflectance of at least 80% in the infrared and/or the visible and/or in the ultraviolet frequency range.

In Example 19, the subject matter of Example 18 can optionally include that the optically opaque material has a reflectance of at least 90% in the infrared and/or the visible and/or in the ultraviolet frequency range.

In Example 20, the subject matter of any one of Examples 1 to 19 can optionally include that the housing includes a substrate on which the acoustic wave sensor is mounted, and a lid.

In Example 21, the subject matter of Example 20 and of any one of Examples 7 to 19 can optionally include that the lid includes a layered portion.

In Example 22, the subject matter of any one of Examples 20 or 21 can optionally include that at least a part of the substrate facing to the inside of the housing is coated with a thermally insulating substrate material.

In Example 23, the subject matter of Example 22 can optionally include that the thermal conductivity of the thermally insulating substrate material is less than 20 W/(m·K).

In Example 24, the subject matter of Example 23 can optionally include that the thermal conductivity of the thermally insulating substrate material is less than 10 W/(m·K).

In Example 25, the subject matter of Example 24 can optionally include that the thermal conductivity of the thermally insulating substrate material is less than 5 W/(m·K).

In Example 26, the subject matter of any one of Examples 20 to 25 can optionally include that the substrate includes an electronic circuit mounted thereon inside the housing. The electronic circuit is at least in part coated with the thermally insulating substrate material.

In Example 27, the subject matter of Example 26 can optionally include that the thermally insulating substrate material is coated on a surface of at least one of a printed circuit board, of an electronic component, a membrane of the acoustic wave sensor, and of a bonding wire.

In Example 28, the subject matter of any one of Examples 1 to 27 can optionally include that the acoustic wave sensor is configured as a microphone.

In Example 29, the subject matter of any one of Examples 1 to 28 can optionally include that the housing wall includes an optically transparent window portion providing an optical port to the inside of the housing.

In Example 30, the subject matter of any one of Examples 1 to 29 can optionally include that the thermally insulating material and/or the thermally insulating substrate material is selected from glass materials, plastic materials, and oxides.

In Example 31 the subject matter of any one of Examples 1 to 30 can optionally include that the housing wall comprises a portion extending from the inner surface to the outer surface of the housing wall, the portion being entirely made of the thermally insulating material.

Example 32 is a device for detecting acoustic waves. The device may include a housing having a metal housing portion, a layer formed on an inner surface of the metal housing portion, and an acoustic wave sensor provided at least partially inside the housing and configured to detect acoustic waves. The layer is made of a material having a thermal conductivity that is smaller than the thermal conductivity of the metal housing portion.

Example 33 is a device for detecting acoustic waves. The device may include a housing having a housing wall with an inner surface and an outer surface, and an acoustic wave sensor provided at least partially inside the housing and configured to detect acoustic waves. The housing wall includes a portion extending from the inner surface to the outer surface of the housing wall, the portion being entirely made of a thermally insulating material.

In Example 34, the subject matter of Example 33 can optionally include that the thermal conductivity of the thermally insulating material is less than 20 W/(m·K).

In Example 35, the subject matter of Example 34 can optionally include that the thermal conductivity of the thermally insulating material is less than 10 W/(m·K).

In Example 36, the subject matter of Example 35 can optionally include that the thermal conductivity of the thermally insulating material is less than 5 W/(m·K).

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A device for detecting acoustic waves, comprising:
a housing having a housing wall with an inner surface, wherein the housing comprises a substrate, the substrate having a first surface facing the inner surface of the housing wall and a second surface opposite to the first surface, wherein a space within the housing is defined between the inner surface of the housing wall and the first surface of the substrate; and
an acoustic wave sensor provided at least partially inside the housing and configured to detect acoustic waves, the acoustic wave sensor mounted on the first surface of the substrate within the space;
wherein the inner surface of the housing wall is made in at least half of its entire area of a thermally insulating material,
wherein the housing wall comprises a layered portion comprising a plurality of layers stacked in a thickness direction of the housing wall;
wherein the layered portion comprises an inner layer forming at least a part of the inner surface of the housing wall, and at least one outer layer positioned closer to an outer surface of the housing wall than the inner layer
wherein the inner layer is made at least in part of a material which is optically transparent.

2. The device of claim 1, wherein the thermal conductivity of the thermally insulating material is less than 20 W/(mK).

3. The device of claim 1, wherein the inner surface of the housing wall is made in at least 70% of its entire area of the thermally insulating material.

4. The device of claim 1, wherein the inner layer is made at least in part of the thermally insulating material.

5. The device of claim 4, wherein at least one outer layer is made at least in part of a material having a higher thermal conductivity than the material of the inner layer;
wherein optionally one outer layer forming at least a part of the outer surface of the housing wall has a higher thermal conductivity than the inner layer.

6. The device of claim 5, wherein at least one outer layer is made at least in part of a metal.

7. The device of claim 1, wherein the optically transparent material is optically transparent in at least one of the following frequency ranges:
the infrared frequency range;
the visible frequency range;
the ultraviolet frequency range.

8. The device of claim 7, wherein the optically transparent material has a transmittance of at least 80% in at least one of the following frequency ranges:
the infrared frequency range;
the visible frequency range;
the ultraviolet frequency range.

9. The device of claim 1, wherein at least one outer layer is made at least in part of a material which is optically opaque.

10. The device of claim 9, wherein the optically opaque material is optically opaque in at least one of the following frequency ranges:
the infrared frequency range;
the visible frequency range;
the ultraviolet frequency range.

11. The device of claim 10, wherein the optically opaque material has a reflectance of at least 80% in at least one of the following frequency ranges:
the infrared frequency range;
the visible frequency range;
the ultraviolet frequency range.

12. The device of claim 1, wherein the housing comprises a lid.

13. The device of claim 12, wherein the lid comprises a layered portion.

14. The device of claim 12, wherein at least a part of the substrate facing the inside of the inner surface of the housing wall is coated with a thermally insulating substrate material.

15. The device of claim 14, wherein the thermal conductivity of the thermally insulating substrate material is less than 20 W/(mK).

16. The device of claim 1, wherein the substrate comprises an electronic circuit mounted on the first surface of the substrate within the space of the housing,
wherein the electronic circuit is at least in part coated with a thermally insulating substrate material.

17. The device of claim 1, wherein the acoustic wave sensor is configured as a microphone.

18. The device of claim 1, wherein the housing wall comprises an optically transparent window portion providing an optical port to the inside of the housing.

19. The device of claim 14, wherein at least one of the thermally insulating material or the thermally insulating substrate material is selected from glass materials, plastic materials, and oxides.

20. The device of claim 1, wherein the housing wall comprises a portion extending from the inner surface to the outer surface of the housing wall, the portion being entirely made of the thermally insulating material.

21. The device of claim 16, wherein the electronic circuit and the acoustic sensor are disposed adjacent to each other in a lateral direction, the lateral direction being parallel to the first surface of the substrate.

22. The device of claim 21, wherein the electronic circuit and the acoustic sensor are mounted directly to the first surface of the substrate.

23. The device of claim 1, wherein the inner layer is made entirely of a material which is optically transparent.

24. The device of claim 9, wherein at least one outer layer is entirely of a material which is optically opaque.

* * * * *